United States Patent
Citterio et al.

(10) Patent No.: US 12,005,178 B2
(45) Date of Patent: Jun. 11, 2024

(54) SURGICAL ASSEMBLY FOR OCULAR SURGERY AND METHOD OF COMPENSATION OF INTRAOCULAR PRESSURE

(71) Applicant: ELECTRONIC SYSTEMS S.P.A., Momo (IT)

(72) Inventors: Roberto Citterio, Masate (IT); Antonio Farago', Novara (IT); Guido Santus, Locate di Triuizi (IT)

(73) Assignee: ELECTRONIC SYSTEMS S.P.A., Momo (IT)

( * ) Notice: Subject to any disclaimer, the term of this patent is extended or adjusted under 35 U.S.C. 154(b) by 644 days.

(21) Appl. No.: 17/079,218

(22) Filed: Oct. 23, 2020

(65) Prior Publication Data

US 2021/0038431 A1     Feb. 11, 2021

Related U.S. Application Data

(62) Division of application No. 15/554,229, filed as application No. PCT/IB2016/051163 on Mar. 2, 2016, now Pat. No. 10,842,672.

(30) Foreign Application Priority Data

Mar. 3, 2015   (IT) .............................. BG2015A0012

(51) Int. Cl.
*A61M 1/00*     (2006.01)
*A61B 3/16*     (2006.01)
(Continued)

(52) U.S. Cl.
CPC ................. *A61M 1/77* (2021.05); *A61B 3/16* (2013.01); *A61B 90/30* (2016.02); *A61F 9/007* (2013.01); *A61F 9/00781* (2013.01); *A61M 1/777* (2021.05); *A61M 1/85* (2021.05); *A61M 3/0216* (2014.02); *A61B 3/0008* (2013.01); *A61B 17/34* (2013.01); *A61B 2090/033* (2016.02); *A61B 2090/036* (2016.02); *A61B 2090/064* (2016.02); *A61M 2205/3344* (2013.01); *A61M 2205/587* (2013.01); *A61M 2210/0612* (2013.01)

(58) Field of Classification Search
CPC ................ A61F 9/007; A61F 9/00781; A61M 2210/0612; A61M 1/77; A61M 2210/061
See application file for complete search history.

(56) References Cited

U.S. PATENT DOCUMENTS 5,676,650 A    10/1997   Grieshaber
5,865,764 A    2/1999    Moorhead
(Continued)

FOREIGN PATENT DOCUMENTS

EP          0180317 A1    5/1986

*Primary Examiner* — Tiffany Legette
(74) *Attorney, Agent, or Firm* — ArentFox Schiff LLP; Michael Fainberg

(57) ABSTRACT

A surgical assembly for ocular surgery includes a direct measuring device of intraocular pressure, a surgical accessory utilisable in conjunction with a surgical instrument suitable for performing eye surgery, and the surgical accessory being insertable in an ocular cavity through an accessory ocular incision. The direct measuring device of intraocular pressure is coupled to the surgical accessory so as to be insertable in the ocular cavity along with the surgical accessory through the accessory ocular incision.

8 Claims, 9 Drawing Sheets

(51) Int. Cl.
   *A61B 90/30*   (2016.01)
   *A61F 9/007*   (2006.01)
   *A61M 3/02*    (2006.01)
   *A61B 3/00*        (2006.01)
   *A61B 17/34*       (2006.01)
   *A61B 90/00*       (2016.01)

(56) References Cited

U.S. PATENT DOCUMENTS

| | | |
|---|---|---|
| 5,910,110 A | 6/1999 | Bastable |
| 8,430,840 B2 | 4/2013 | Nazarifar |
| 2006/0149194 A1 | 7/2006 | Conston |
| 2008/0082078 A1* | 4/2008 | Berlin ............... A61F 9/0017 |
| | | 604/521 |
| 2011/0118729 A1 | 5/2011 | Eeren |
| 2014/0171991 A1 | 6/2014 | Lee |
| 2014/0194834 A1 | 7/2014 | Passaglia |
| 2015/0148836 A1* | 5/2015 | Heeren ............... A61B 3/16 |
| | | 606/170 |

* cited by examiner

SURGICAL ASSEMBLY FOR OCULAR SURGERY AND METHOD OF COMPENSATION OF INTRAOCULAR PRESSURE

CROSS-REFERENCE TO RELATED APPLICATIONS

This application is a divisional application of U.S. application Ser. No. 15/554,229, filed on Aug. 29, 2017, entitled "SURGICAL ASSEMBLIES FOR OCULAR SURGERY, SYSTEMS AND METHODS OF COMPENSATION OF INTRAOCULAR PRESSURE," which is a U.S. National Phase of Application No. PCT/IB2016/051163, filed Mar. 2, 2016, which claims priority to Italian Application No. BG2015A000012, filed Mar. 3, 2015, and which is incorporated in its entirety by reference herein.

TECHNICAL FIELD

The present invention relates to a surgical assembly for ocular surgery, in particular suitable to perform a direct measurement of intraocular pressure.

BACKGROUND

During eye surgery which involves manipulation of the eyeball, the infusion of fluids, fragmentation and aspiration of ocular tissue, there can substantial variations of pressure in the eye treated. Clinical studies have shown that in vitrectomy operations for the removal of the vitreous body, intraocular pressure may vary between 0 and 120 mmHg. In phacoemulsification operations for cataract extraction and fragmentation, pressure values of over 60 mmHg have been registered, corresponding to retinal perfusion pressure. Significant pressure variations have also been measured following manipulation manoeuvres of the eyeball in scleral indentation operations to treat retinal detachment, with peaks of up to 210 mmHg in the case of external pressure applied to the sclera.

Intraocular pressure changes can increase the risk of intraoperative and postoperative complications, such as expulsive haemorrhage, choroidal detachment and retinal ischemia. Expulsive haemorrhage and choroidal detachment may be associated with pressure drops during the operating phase. Prolonged increases in intraocular pressure can instead result in a reduction of vascular perfusion pressure resulting in impairment of the blood flow to the optic nerve and to the retina. Pressure variations may also adversely affect the recovery of eye function after surgery. In fact, it has been shown that transient increases of ocular perfusion pressure may lead to morphological and functional alterations of the retina. The effects of changes in intraocular pressure on sight may be especially harmful to patients with impaired ocular perfusion, caused for example by diabetic retinopathy.

The monitoring of intraoperative changes in intraocular pressure is therefore crucial to ensure the safety and efficacy of surgical operations.

Various devices and methods for measuring intraocular pressure have been proposed. U.S. Pat. No. 4,841,984 and US 2008/082078 describe devices that are based on the direct measurement of intraocular pressure using a pressure transducer integrated in the surgical instrument inserted in the eye cavity, which is used for the infusion of fluid or the fragmentation and removal of eye tissue. A control circuit is also present which automatically adjusts the infusion or aspiration of the instrument in response to the intraocular pressure measured, keeping it within a safe range. A first limit of such devices is the need for a larger incision of the eye for the insertion of the integrated transducer and instrument. A further disadvantage is the proximity of the transducer to the surgical instrument, the use of which inevitably causes disturbance and inaccuracies in the measurement of intraocular pressure.

To overcome these limitations different approaches have been proposed based on the indirect estimation of intraocular pressure starting from measurement of the pressure or flow on the infusion/aspiration line of the surgical instrument using a remote transducer.

U.S. Pat. Nos. 5,865,764 and 8,430,840 describe devices using one or two pressure or flow sensors placed outside the eye cavity on the infusion/suction line inserted in the anterior chamber or vitreous body of the eye. Intraocular pressure is obtained by means of a calibration procedure starting from the measurement of pressure or flow by the remote sensors.

U.S. Pat. No. 5,910,110 describes a device in which the pressure transducer inserted instead in the reservoir connected to the infusion/aspiration system measures the deflection of a diaphragm caused by the fluid in the reservoir, thus ensuring isolation between the transducer and irrigation fluid.

The disadvantage of the indirect systems described above mainly consists of the possibility of measuring intraocular pressure only in the presence of infusion or aspiration of fluids by the surgical instrument. Such systems are not able to detect changes in pressure caused by external factors, such as the injection of other fluids (epiretinal membrane dyes, vitreous substitutes) or manipulations of the eyeball (scleral indentation, insertion or removal of the surgical instruments). Intraocular pressure readings estimated indirectly using sensors on the infusion line were compared with the direct measurement obtained from intraocular transducers during vitrectomy operations. During infusion or aspiration, the indirect measurement of pressure accurately reproduces direct measurement. However, pressure changes caused by movement of the surgical instruments and the scleral pressures exerted externally are not detected with the indirect method.

The current clinical procedure of trabeculectomy for glaucoma treatment does not provide for any intraoperative monitoring system of intraocular pressure. Surgical instruments for vitrectomy or cataracts operations are instead equipped with pressure monitoring systems. The first systems were based on the force of gravity or forced pressurised air infusion. In the latest generation instruments, such as the Constellation Vision System for vitrectomy and the Centurion Vision System for cataract operations (Alcon, Fort Worth, Texas, USA), control of the intraocular pressure based on an active flow balance has been introduced. The flow measured on the aspiration and infusion line of the instrument is used to indirectly estimate intraocular pressure changes and maintain the desired pressure value. Systems with active flow balance make it possible to mitigate the intraocular pressure changes caused by the operations of the surgical instrument, but are unable to compensate for pressure variations related to external factors. During the cutting and aspiration step of the vitreous body pressure decreases were recorded of about 7 and 18 mmHg, which were then compensated in 2.6 seconds. During scleral indentation instead rapid pressure increases up to 70-100 mmHg were recorded, recovered slowly in about 4 seconds.

Currently, as far as we know, there are no instruments on the market for eye surgery which integrate direct measurement of intraocular pressure.

US 20110118729 A1 describes a vitrectome coupled to a control circuit with the aim of enabling or disabling the instrument on the basis of the physical parameter measured. Among these parameters may be intraocular pressure, which is used to check whether the victrectome is correctly positioned inside the eye cavity. To be able to activate the victrectome in fact, the measured pressure must be equal to the infusion pressure of the fluid, but there is no control over the pressure variations compared to the set pressure.

US 20140171991 A1 describes a victrectome fitted instead with a pressure transducer to control the output pressure of the cutting instrument, but in this case too no direct monitoring of intraocular pressure is performed.

US 2014194834 A1 describes a device for controlling pressure in the eye which consists of four elements: a positioning cannula (housed in the anterior chamber of the eye), a two-way pump (infusion/aspiration), a control circuit and a pressure sensor housed inside the pump reservoir and suitable to measure the pressure of the fluid in the reservoir. This device is thus provided with an indirect measuring system, which allows the measurement of intraocular pressure only in the presence of fluid infusion or aspiration. This system does not however permit the measurement of pressure variations caused by external factors or manipulations of the eyeball.

US 2006/149194 describes a system for treating eye disease which includes a micro-cannula inside which a single inner element can be slidingly inserted, designed to come out of the distal end of the micro-cannula. The inner element can be used for the transport of fluids or sensors.

There is a need to provide a direct measurement of intraocular pressure without the aforementioned disadvantages n relation to the prior art.

SUMMARY

A purpose of the present invention is to reduce the intraoperative and postoperative complications of surgery, making it possible to monitor and adequately compensate intraocular pressure changes associated with operations inside the anterior or vitreous chamber, such as the fragmentation of eye tissue, aspiration of the fragments and infusion of fluids, particularly in eye surgery such as trabeculectomy, phacoemulsification, vitrectomy and scleral indentation.

A further purpose of the invention is to limit the number of ocular incisions and minimise the size of the incisions, to make the direct measurement of the pressure less invasive and more tolerable for the patient.

Such purposes are achieved by a surgical assembly for ocular surgery according to claim 1, a compensation system of intraocular pressure according to claim 12, a direct measurement method of intraocular pressure according to claim 19, and a compensation method of intraocular pressure according to claim 22. The dependent claims describe preferred embodiments of the invention.

A surgical assembly for ocular surgery is proposed comprising a direct measuring device of intraocular pressure and a surgical accessory utilisable in conjunction with a surgical instrument suitable to perform eye surgery where said surgical accessory is insertable in the ocular cavity through an accessory ocular incision. Accessory ocular incision is understood to mean, in the context of this description, an incision made in the anterior chamber or vitreous chamber of the eyeball to insert a surgical accessory in the eyeball and which is therefore distinct from the incision through which the surgical tool itself operates.

The direct measuring device of intraocular pressure is coupled to the surgical accessory so as to be insertable in the ocular cavity along with said surgical accessory through said accessory ocular incision.

In a preferred embodiment, the surgical accessory is an endoilluminator for the illumination of the field of surgical action for example in vitrectomy operations.

In a preferred embodiment, the surgical accessory is an infusion cannula of an infusion system, suitable for injecting an irrigation fluid for a compensation of intraocular pressure.

In some advantageous embodiments, the measurement device comprises a fiber-optic pressure transducer.

In some preferred embodiments, the endoilluminator comprises an optic fiber and a chandelier probe.

In some preferred embodiments, the optic fiber pressure transducer and endoilluminator are coupled to each other by an attachment guide ring in which the transducer and endoilluminator, placed alongside each other, are inserted with interference. The attachment guide ring is suitable to abut with a flange of a positioning cannula, such as a valved cannula, positioned in the eyeball to determine the insertion depth of the pressure transducer and endoilluminator in the eyeball.

In some preferred embodiments, in which the surgical accessory is an infusion cannula, the optic fibre pressure transducer extends inside the infusion cannula.

In some embodiments, in which the surgical accessory is an infusion cannula, the infusion cannula consists of a distal portion suitable to be inserted in the eyeball and a cylindrical proximal portion suitable to abut with a flange of a positioning cannula, such as a valved cannula, positioned in the eyeball and suitable to receive the distal portion of the infusion cannula with the pressure transducer inserted.

In some embodiments, in which the surgical accessory is an infusion cannula, the pressure transducer and the infusion cannula are connected to each other by a three-way valve, a first way being fluidically connected to the infusion cannula, a second way, aligned with the first, being connected to a pressure transducer which crosses the valve to insert itself in the infusion cannula; a third way is fluidically connected to an output line of a fluid infusion pump.

In some embodiments, the infusion pump can also be used in aspiration to reduce intraocular pressure in the case in which the vitreous body is not present inside the eye.

The pressure transducer is provided, at some distance from its distal end, with an attachment guide that works in conjunction with the second way of the three-way valve in order to lock the position of the transducer so that its distal end protrudes to the desired extent beyond the distal end of the infusion cannula.

Advantageously, the position of the pressure transducer is set up in such a way that its distal end is at a greater depth than the distal end of the infusion cannula to prevent the pressure measurement from being disturbed by the infusion of fluids.

The three-way valve can be controlled, for example in manual mode or by means of an electrical signal sent by a control unit, to place the first way in fluidic communication with the third way, so as to allow the passage of an infusion fluid from the output line of the infusion pump to the infusion cannula or the aspiration of intraocular fluid.

In some preferred embodiments, a compensation system of the intraocular pressure comprises a control unit suitable to receive a pressure signal coming from the measuring device and to compare a pressure value derivable from such pressure signal with a preset pressure range.

In one embodiment, the control unit is programmed to generate an alarm signal if the pressure value measured is higher than a maximum pressure value allowed or lower than a minimum pressure value allowed.

In a further embodiment, the control unit is programmed to control a pressure compensation circuit. For example, the control unit is suitable to control the infusion pump and the three-way valve in order to send an infusion fluid from a reservoir of fluid to the infusion cannula.

In one embodiment, the control unit is suitable to control the infusion pump and the three-way valve in order to aspirate the intraocular fluid to reduce intraocular pressure.

BRIEF DESCRIPTION OF THE DRAWINGS

Further characteristics and advantages of the invention will, in any case, be evident from the description given below of its preferred embodiments, made by way of a non-limiting example with reference to the appended drawings, wherein:

FIGS. 4 and 4a show, in elevation and in axial cross-section, the surgical assembly of the previous figure inserted in a valved cannula;

DETAILED DESCRIPTION

Figure 1:
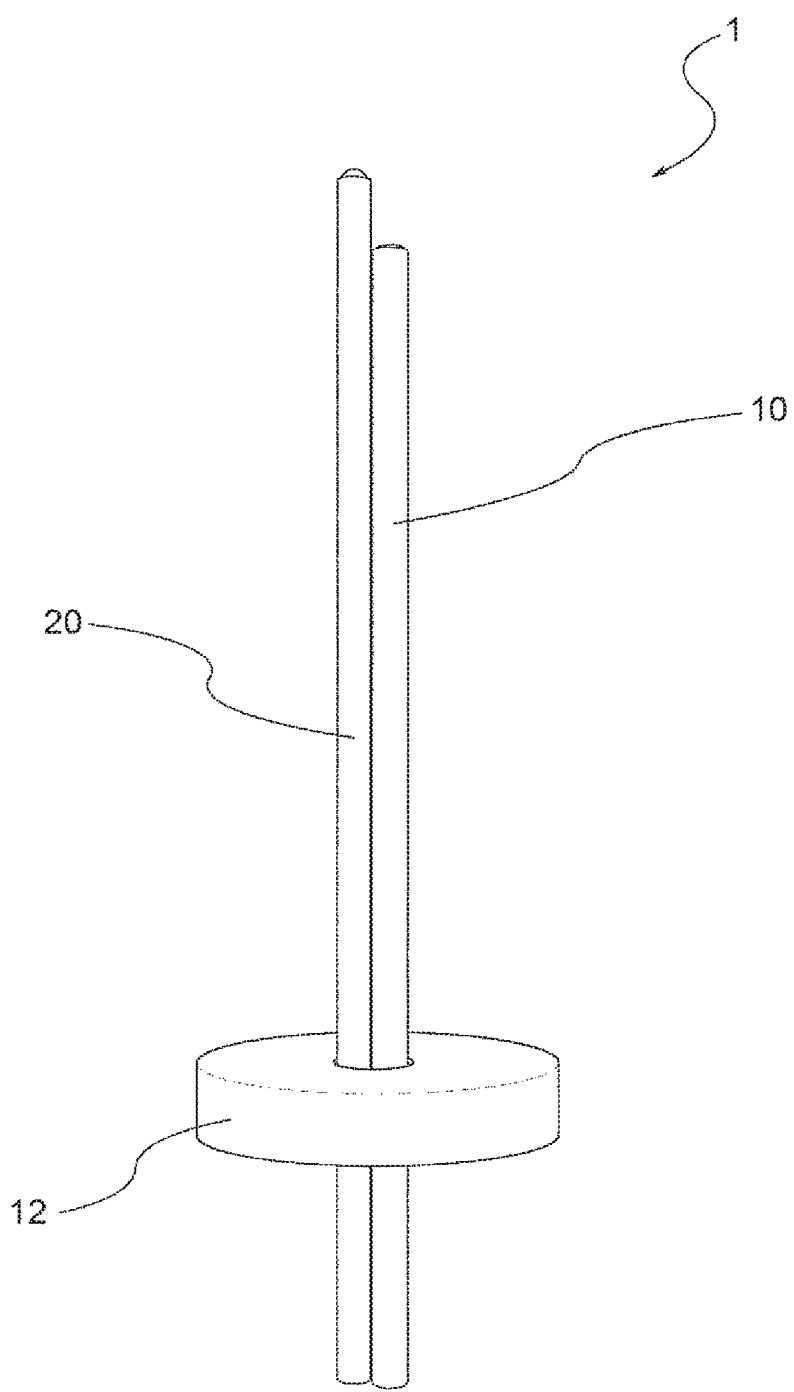
FIG. 1 shows a surgical assembly according to the invention, in an embodiment comprising a measuring device of the pressure coupled to an endoilluminator.

In some embodiments, the surgical assembly consists of three modules, combined as described below. The three modules have the following functions: direct measurement of intraocular pressure, illumination and infusion of fluids. Advantageously, the surgical assembly according to the invention uses a single ocular incision for the contemporary insertion of two different modules, coupled according to the specific requirements for the various surgical operations. This approach makes it possible to integrate in a single device both the basic functionality required during eye surgery, such as lighting or infusion, and functions not found in current surgical instruments, such as the direct measurement of intraocular pressure changes, requiring a single ocular incision of limited size. Hereafter, such ocular incision will also be referred to as accessory incision to distinguish it from the incision through which the surgical tool itself operates.

For example, the assembly according to the invention provides for a single accessory ocular incision made by using a needle with external diameter of not more than 0.5 mm, in order to reduce postoperative complications of surgery and speed up patient recovery.

A first module used to obtain the surgical assembly according to the invention is the pressure detector 10, i.e. a miniaturised pressure transducer for the direct measurement of intraocular pressure.

In advantageous embodiments, the pressure detector 10 is a fiber optic transducer which transmits the pressure signal obtained from the deflection of a diaphragm in the form of a variation in the intensity of the light reflected through a fiber optic. The advantages of this type of transducer are related to its small dimensions and the absence of voltages for signal transmission. A commercial example of a fiber optic pressure transducer is the product Fiber Optic Pressure Sensor OPP-M25 manufactured by Opsens (Quebec, Canada). This sensor has an outside diameter of 0.25 mm and a measuring accuracy of ±2 mmHg in a range of pressures from −30 to +300 mmHg. The pressure detector 10 is connected to a conditioning unit 12 (shown schematically in FIGS. 8 and 9) for capturing and amplifying the pressure signal at a frequency up to 250 Hz.

A second module used to obtain an assembly according to the invention comprises an endoilluminator 20, needed in vitrectomy operations to illuminate the field of surgical action. The lighting can be obtained either through fiber optic systems which can be directed by the surgeon depending on the ocular area of interest, or by means of chandelier probes inserted in the eye cavity in a fixed position and anchored to the outer surface of the sclera with a special guide.

The invention provides, in particular, for the use of lighting systems with a diameter not exceeding 0.25 mm to be compatible with the size of the needle and the pressure detector. For example, the fibre contained in the chandelier Oshima Dual of Synergetics (O'Fallon, Missouri) may be used.

A third module which can be used to obtain an assembly according to the invention has an infusion system 30 needed to compensate the depression measured by the measuring device. This module includes a reservoir 32 containing the irrigation fluid, such as a physiological saline solution compatible with the intraocular fluid. In some embodiments, an infusion pump 34 is also present, such as a positive displacement or syringe pump, such as, for example the Alaris products of CareFusion Corporation (San Diego, California, USA), or a peristaltic pump, such as the one marketed by the Watson-Marlow company, which reaches flow rates up to 1200 ml/h. The infusion pump 34 is connected to the reservoir of fluid through an input line while it regulates the amount of fluid on the output line needed to compensate the pressure variations measured.

In some embodiments, the infusion pump 34 or an additional pump, is suitable to operate in aspiration to aspirate intraocular fluid and can be fluidically connected to a second collection reservoir of the aspirated fluid.

In the case in which vitrectomy surgical instruments 100 provided with an infusion line 102 (FIG. 8) are present, the output line of the infusion pump can be connected to a battery of taps 36 presents on the infusion line 102 of the surgical instrument 100, for example a vitrectome, by a three-way valve. In this case, as will be described below in more detail, the pressure detector 10 is coupled to the endoilluminator 20.

In the event that there is no surgical instrument with an infusion line (FIG. 9) present, a connection via a three-way solenoid valve 40 of the output line of the pump 34 to an infusion cannula 50 may be provided for. In this case, the pressure detector 10 is coupled to the infusion cannula 50.

FIG. 1 shows a surgical assembly according to the invention in an embodiment which provides for the combined use of the first and second modules. An optic fiber pressure transducer 10 is coupled to an endoilluminator 20. The two devices side by side are inserted with interference in an attachment guide ring 12. Said attachment guide ring 12 is positioned at a predetermined distance from the ends of the pressure transducer 10 and the endoilluminator 20.

Figure 2:
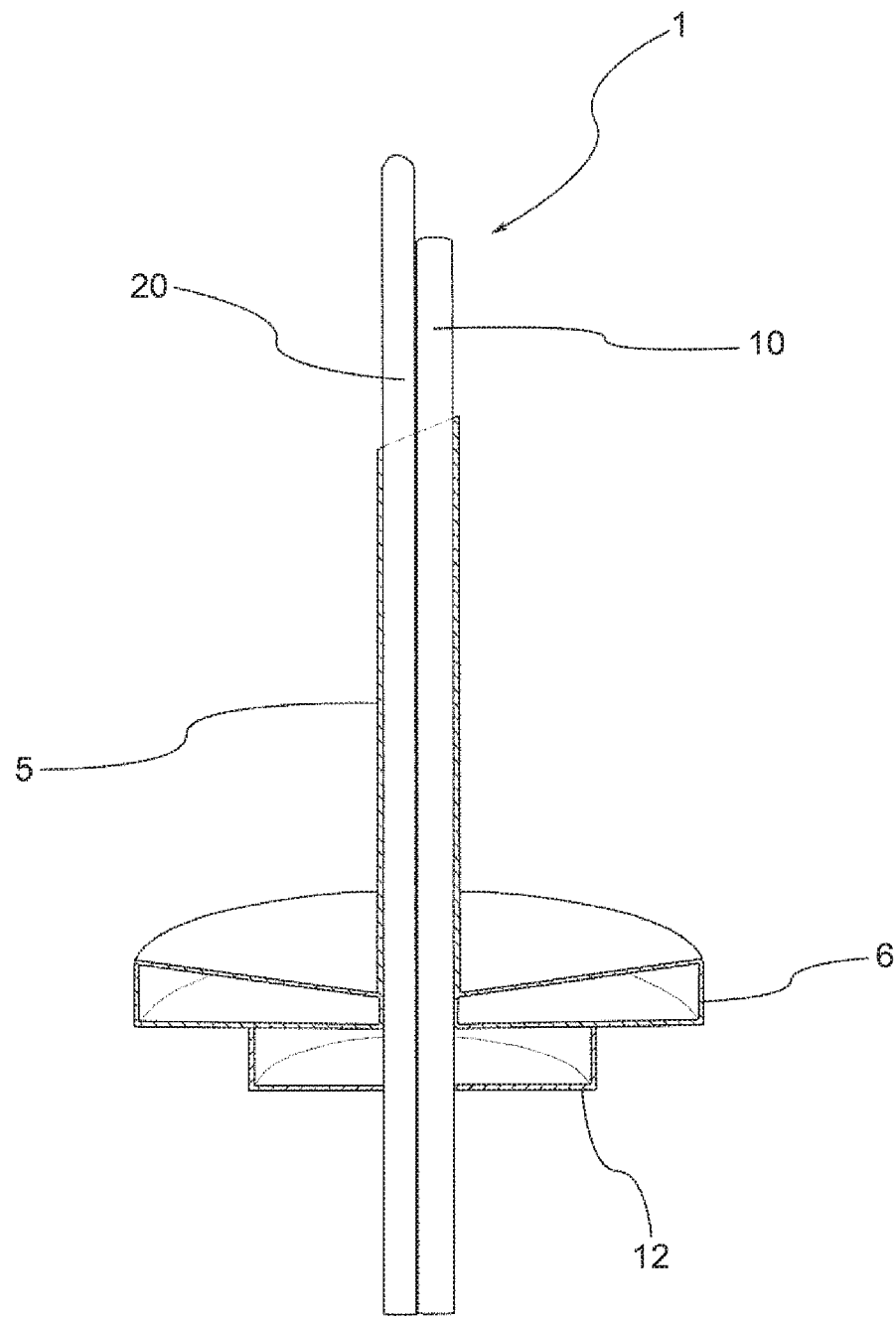
FIG. 2 shows the surgical assembly of the previous figure inserted in a valved cannula.

FIG. 2 shows the surgical assembly 1 inserted in a positioning cannula 5, for example a valved cannula, suitable to be placed in the eye cavity.

In the rest of the description, a valved cannula is understood to mean a positioning cannula fitted with a valve at the end to prevent the leakage of fluids from the ocular incision. The use of a valved cannula is particularly advantageous to be able to work and measure pressure in a closed circuit.

Figure 6:
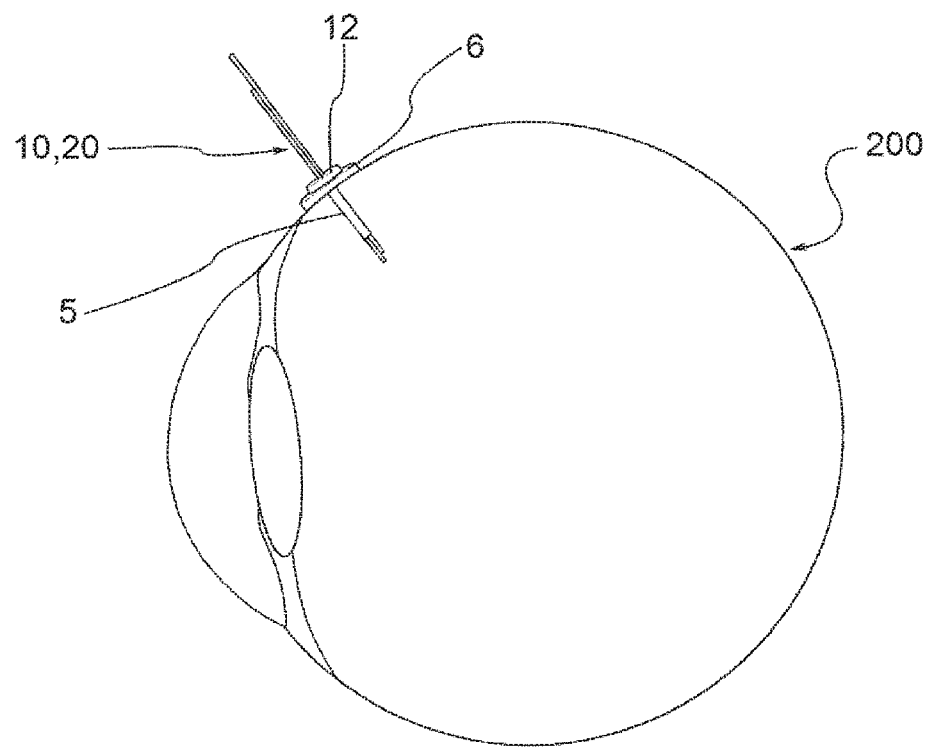
FIG. 6 shows the surgical assembly of FIG. 2 inserted in the vitreous chamber of the eyeball.

As may be noted, the attachment guide ring 12 abuts with the flange 6 of the positioning cannula 5, so as to establish the depth of insertion of the pressure transducer 10 and endoilluminator 20 inside the eye cavity 200, as shown in FIG. 6.

Figure 3:
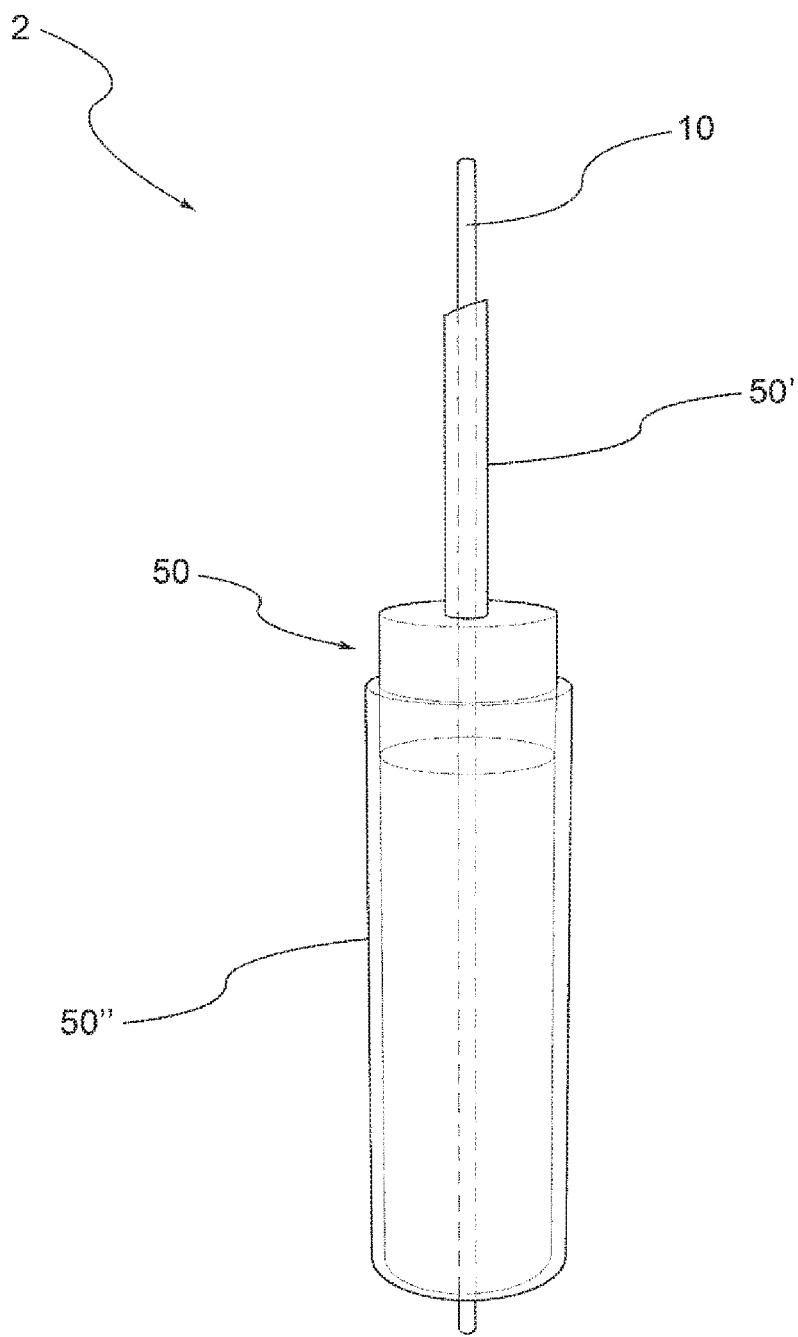
FIG. 3 shows a surgical assembly according to the invention, in an embodiment variant comprising a measuring device of the pressure coupled to an infusion cannula.
Figure 4:
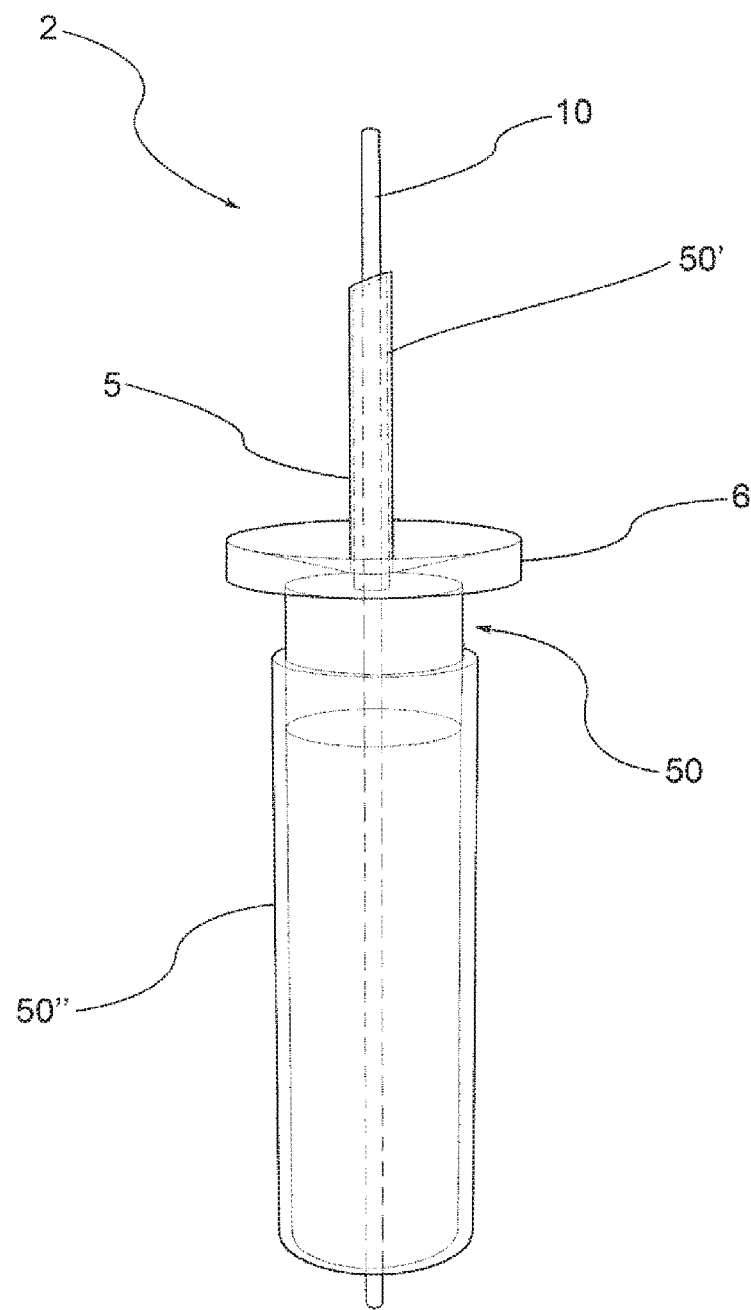

FIG. 3 shows a surgical assembly 2 according to the invention in an embodiment which involves the combined use of the first and third module. In particular, the fiber optic transducer 10 is inserted coaxially in an infusion cannula 50. The latter comprises a distal portion 50' suitable to be inserted in the eye cavity and a proximal cylindrical portion 50" suitable to abut with the flange 6 of the positioning cannula 5 for example a valved cannula. The distal portion 50' of the infusion cannula 50 and a distal portion of the transducer 10 are inserted in the positioning cannula as shown in FIG. 4.

For example, as the infusion cannula 50, a "high-flow" cannula of the type sold by the company D.O.R.C. International may be used.

In one embodiment, the pressure detector is inserted with interference in an attachment guide ring 12 cooperating with the infusion cannula 50 so as to determine the position of the distal end of the transducer 10 relative to the distal end of the infusion cannula 50.

Figure 5:
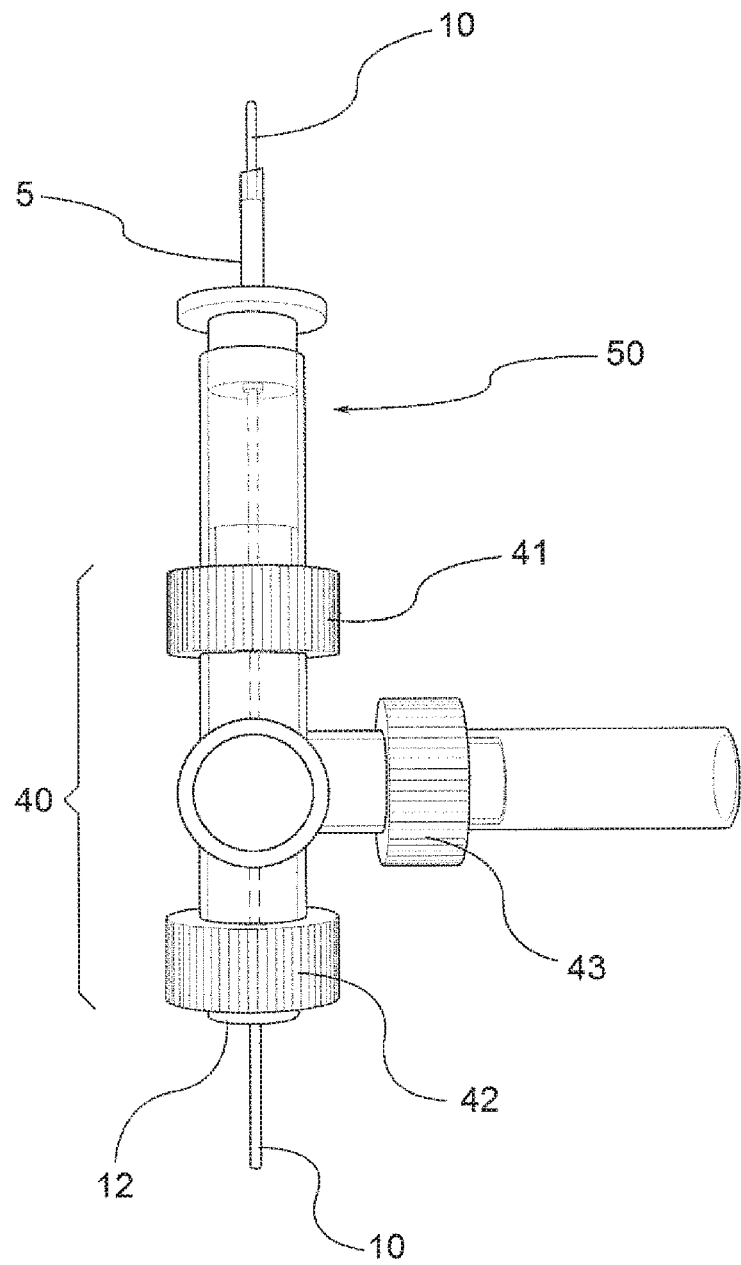
FIG. 5 shows the surgical assembly of the previous figure connected to a three-way valve.

In one embodiment shown in FIG. 5, the pressure detector 10 and infusion cannula 50, with the respective ends inserted in the positioning cannula 5 are connected to each other by a three-way valve 40. A first way 41 is fluidically connected to the infusion cannula 50; a second way 42, aligned with the first, is connected to the pressure detector 10; a third way 43 is fluidically connected to the output line of the infusion pump 34. The attachment guide ring 12 in this case acts in conjunction with the entrance of the second way 42 of the valve 40 to lock the axial position of the pressure detector 10.

Figure 8:
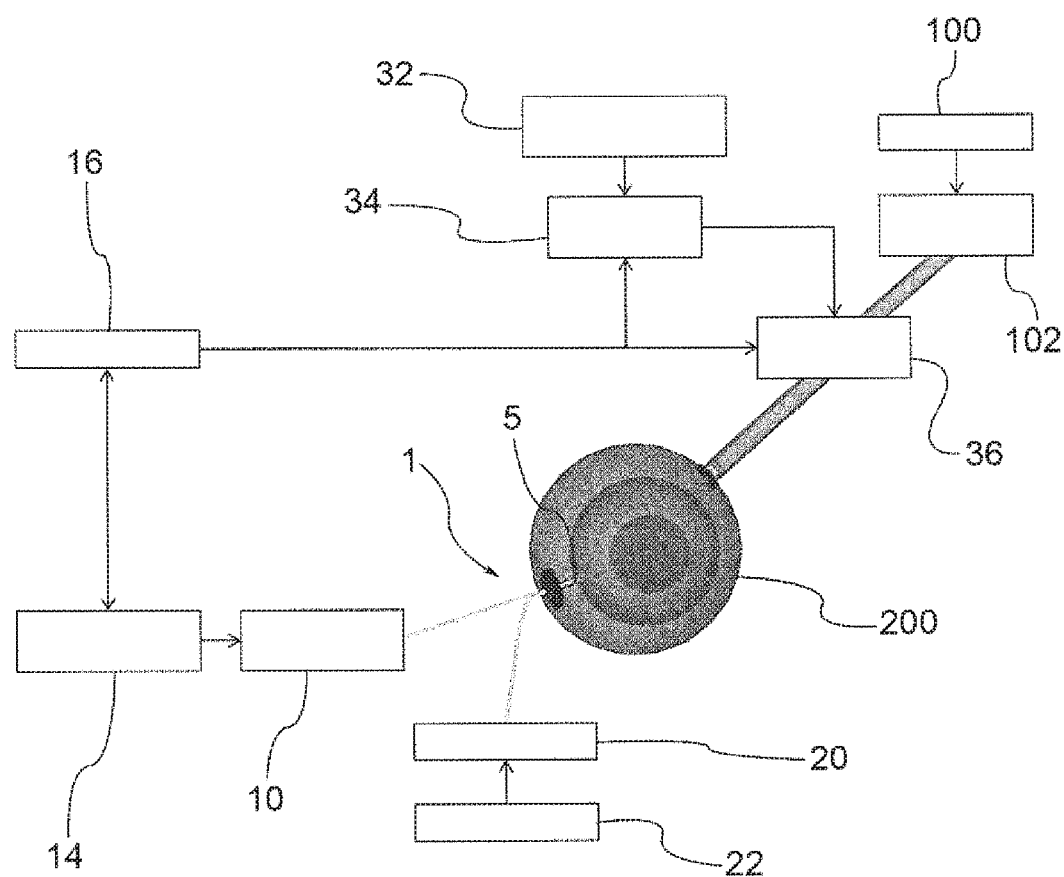
FIG. 8 is a block diagram of a compensation system of ocular pressure in vitrectomy surgery.

FIG. 8 is a block diagram of a compensation system of intraocular pressure in a case of vitrectomy surgery, which uses the surgical assembly 1 composed of the pressure transducer 10 and the endoilluminator 20. The endoilluminator 20 is operatively connected to a light source 22 and is inserted, along with the pressure detector 10 in a positioning cannula 5 positioned in the eyeball 200.

The pressure detector 10 is operatively connected to a conditioning unit of the signal 14, which in turn communicates with a control unit 16 of the compensation system. The control unit 16 controls the operation of an infusion pump 34 and a tap with solenoid valve 36 connected to an infusion cannula 102 of the surgical instrument 100, in this case the vitrectome. The infusion pump 34 is suitable to aspirate the infusion fluid from a reservoir 32 and is connected in output to the tap with solenoid valve 36 of the infusion cannula 102.

Figure 9:
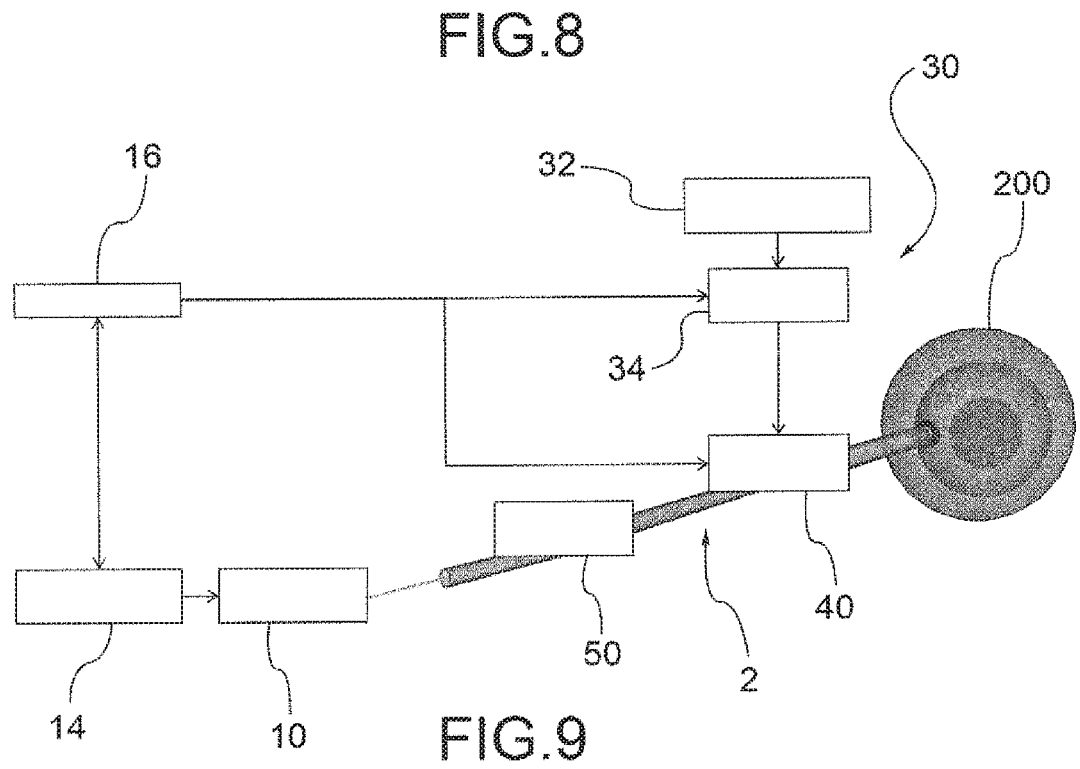
FIG. 9 is a block diagram of a compensation system of ocular pressure in a cataract operation or trabulectomy.

FIG. 9 illustrates instead a pressure compensation system in the case of intraocular cataract surgery or trabeculectomy. The compensation system uses the surgical assembly 2 composed of the pressure detector 10 and the infusion cannula 50, for example in the connection configuration using the three-way valve 40. In this case, the control unit 16 controls, in addition to the infusion pump 34, the tap with three-way valve 40 to which the infusion cannula 50 is connected.

Figure 10:
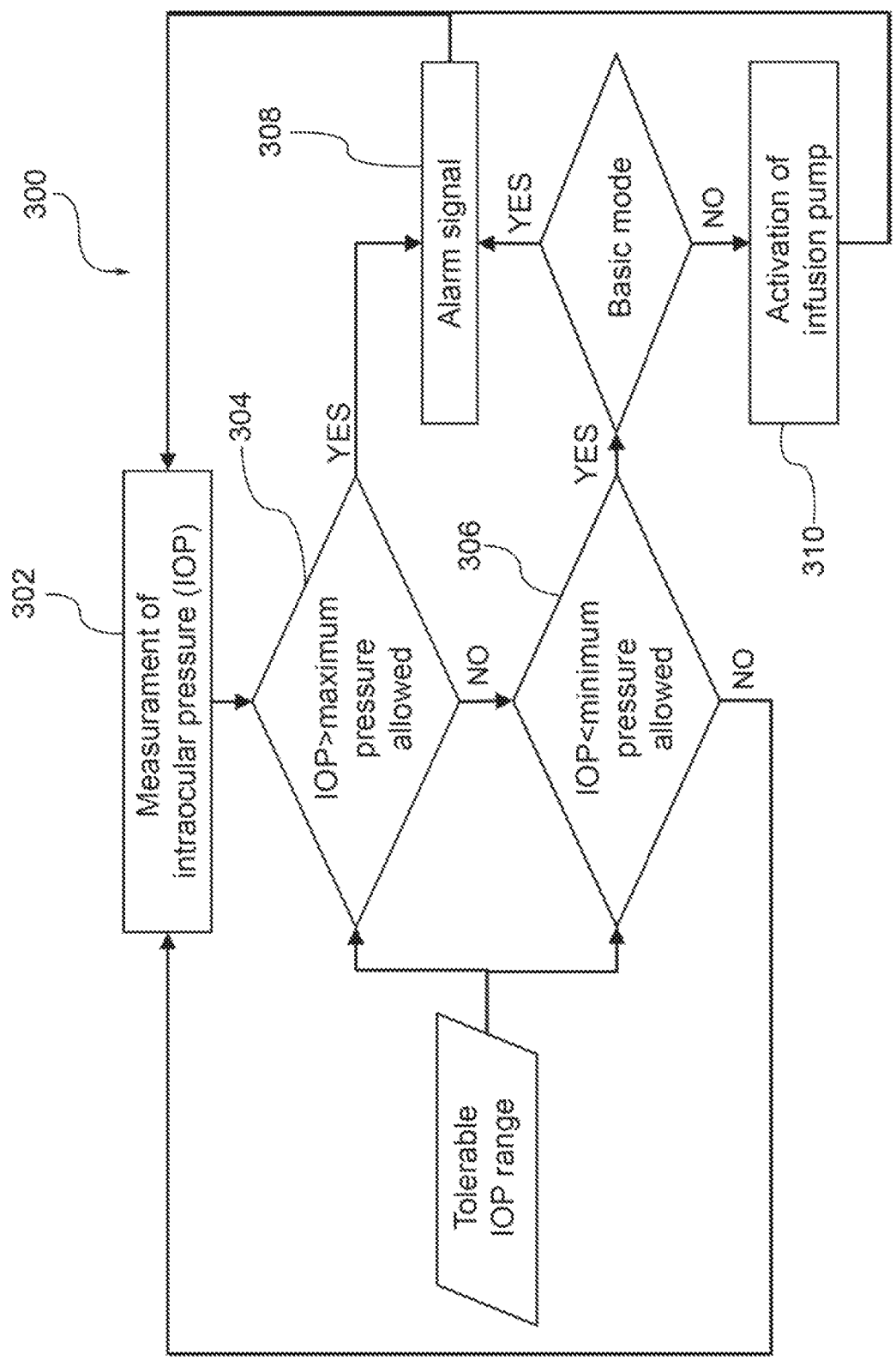
FIG. 10 is a flowchart of a control algorithm of intraocular pressure.

In one embodiment shown in the flow chart in FIG. 10 relative to a compensation algorithm 300 of intraocular pressure, the control unit 16 processes the pressure signal acquired from the transducer (step 302) and compares the pressure value measured with a range of tolerable pressures (steps 304 and 306). Based on the outcome of this comparison, the control unit 16 sends appropriate control signals according to two modes of operation. In the basic mode, the control unit supplies an alarm signal in the form of visual or auditory feedback to the surgeon in the case in which pressure variations are recorded outside the tolerable range (step 308). The possibility of activating the alarm signal only if the pressure values are below threshold or above threshold for a time interval greater than that allowed may also be provided for.

In an optional mode of operation, it instead provides for a compensation in line of the intraocular depressions through automatic or on-demand infusion by the surgeon. In this mode, in the case in which decreases in intraocular pressure below the established threshold are recorded (step 306) the control unit activates the infusion pump in order to compensate for pressure changes automatically or at the surgeon's request (step 310).

Figure 11:
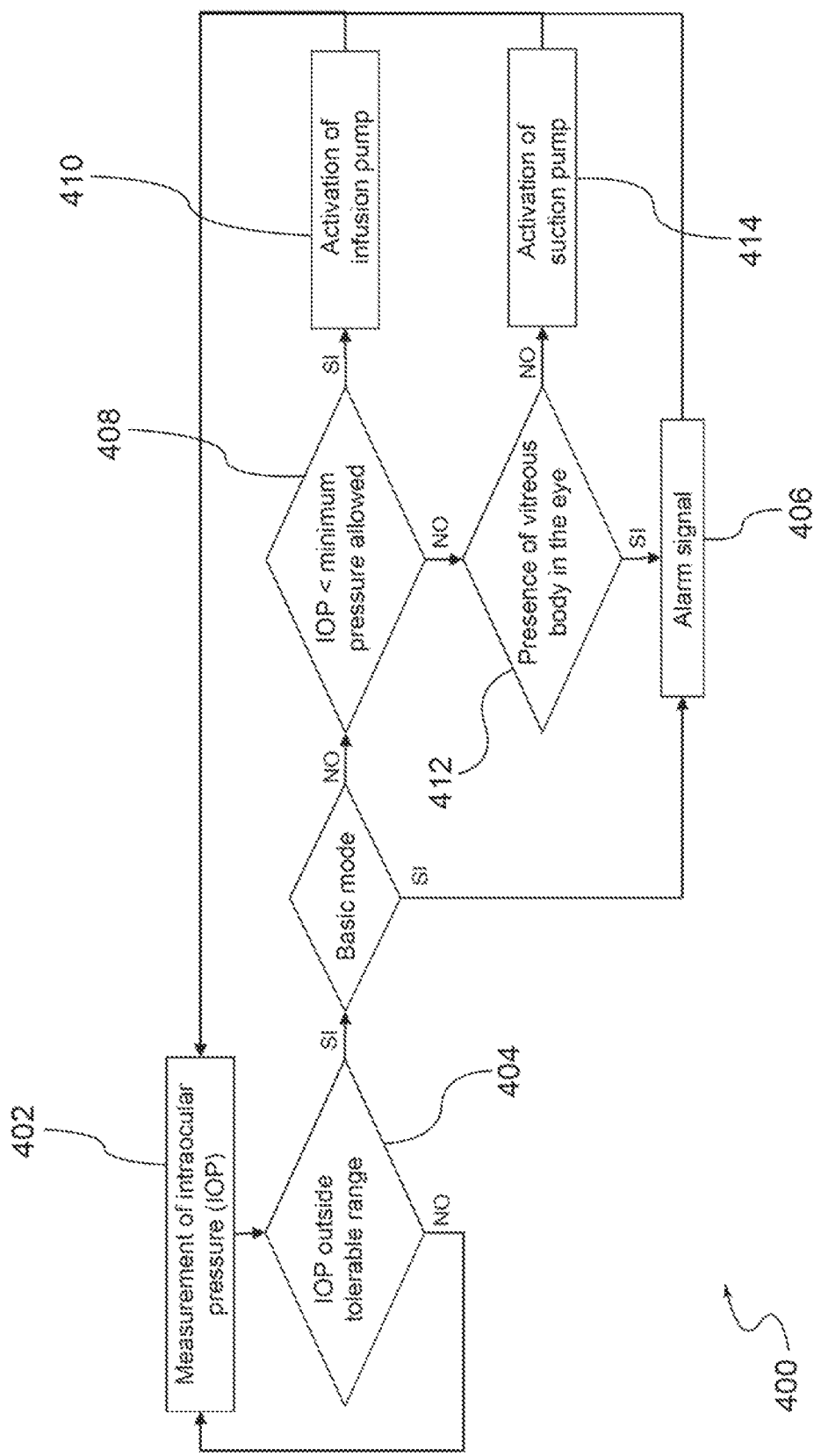
FIG. 11 is a flowchart of a control algorithm of intraocular pressure in an alternative embodiment.

The flowchart in FIG. 11 illustrates a compensation algorithm 400 of intraocular pressure according to an embodiment variant.

The control unit 16 processes the pressure signal acquired by the transducer (step 402) and compares the pressure measured with a tolerable pressure range (step 404). If the pressure measured is not within the tolerable range, and if the control unit 16 operates in a basic mode, the control unit 16 provides an alarm signal in the form of visual or auditory feedback to the surgeon (step 406). The possibility of activating the alarm signal only if the pressure values are below threshold or above threshold for a time interval greater than that allowed may also be provided for.

If the control unit 16 operates in an active control mode and if the pressure is below the minimum threshold (step 408), the control unit 16 activates the pump 34 in infusion to compensate the pressure changes automatically or at the surgeon's request (410).

If the measured pressure exceeds the maximum pressure allowed, and if the vitreous body is not present in the eye, (step 412), then the control unit 16 activates the pump to aspirate the intraocular fluid (step 414).

If instead the vitreous body is present inside the eye, then it simply generates the alarm signal (step 406).

If the vitreous body is present in the eye, in fact, aspiration of the vitreous body should be avoided so as not to cause detachment of the retina.

It is to be noted that, in the case of the pressure compensation procedure providing for aspiration of the intraocular fluid, a special reservoir may be provided which collects the aspirated fluid so as to not contaminate the irrigation fluid.

Moreover, when the pump 34 is active, in infusion or aspiration, the infusion through the vitrectome can be disabled by means of the tap with solenoid valve 36.

Examples of use of the intraocular pressure compensation systems described above will now be given.

Depending on the type of ocular surgery, several possible application scenarios of the invented device are provided for.

As mentioned above, in the case of vitrectomy (FIGS. 6 and 8), the modules inserted in the eye cavity by means of the positioning cannula are represented by the pressure detector 10 and the endoilluminator 20. The output line of the infusion pump 34 is connected to the infusion line 102 of the surgical instrument 100, thus using an access point for the infusion of fluid different from the point of pressure measurement. In the case of measuring increases in pressure, caused for example by indentation or infusion of external fluids, a visual or audible alarm is activated to alert the surgeon and cause him/her to decrease the indentation or the infusion pressure to compensate for the pressure increases.

In a variant described above, in the event of pressure increases automatic aspiration of intraocular fluid by the pump is also possible if the vitreous body is not present in the eye.

In the case in which intraocular depressions are recorded, related for example to the fragmentation and aspiration of tissue, depending on the selected mode of operation the device provides the warning signal or activates the infusion pump and the solenoid valve to which it is connected, to infuse saline solution in the eye cavity and maintain pressure within the acceptable range.

Figure 7:
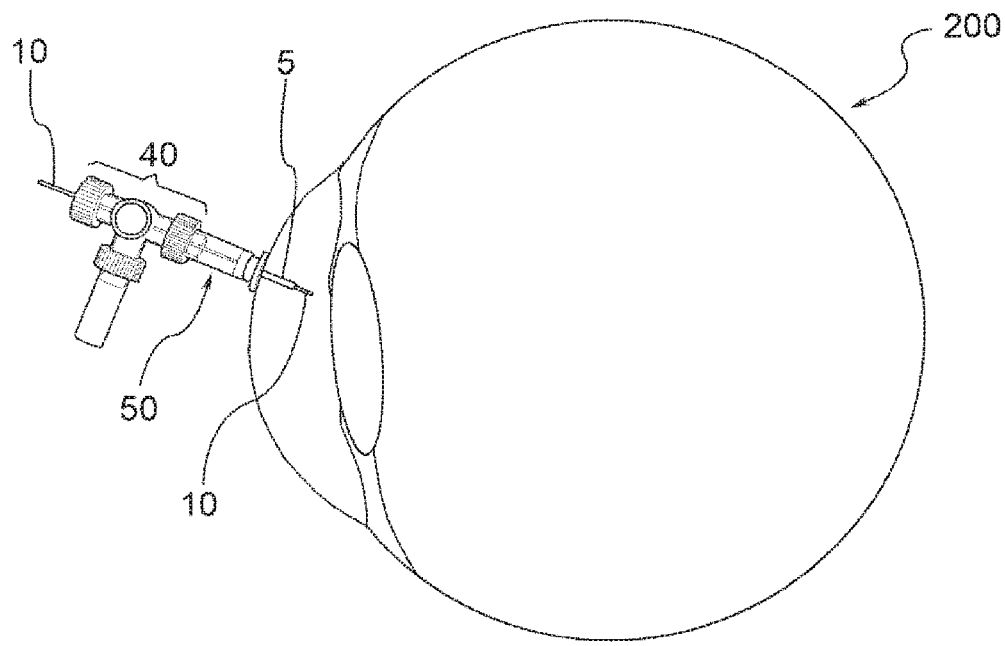
FIG. 7 shows the surgical assembly of FIG. 5 inserted in the anterior chamber of the eyeball.

Trabeculectomy and cataract operations (FIGS. 7 and 9) do not require instead any intraocular illumination system. In this scenario, the modules used are the pressure detector 10, such as the fiber optic transducer, and the infusion system 30. The optic fiber pressure transducer 10 is inserted in the infusion cannula 50 connected to the positioning cannula, to which the output line of the infusion pump is also connected. In the case in which decreases in intraocular pressure below the set value are detected, following for example an excessive outflow of aqueous humour from the anterior chamber of the eye, the device activates the alarm signal or the infusion pump in order to restore the pressure values within the safe range.

With regard to compensation of the intraocular pressure, it must be specified that during vitrectomy surgery in some cases the step of fluid infusion is interrupted by the surgeon and an infusion into the vitreous cavity of air is performed. In this case, the pressure detector continues to operate independently of the administration of fluids or air. In case of exceeding a minimum pressure threshold, the pressure compensation system provides for the intervention of the infusion pump to restore the pressure above the minimum threshold. Since the surgeon is operating while infusing air and the ingress of fluid in the vitreous chamber is not allowed in that it would damage surgery, the solenoid valve which opens the infusion circuit controlled by the infusion pump can no longer be controlled, but another way is opened connected to the external control unit and/or connected to the surgical instrument (in this case the phaco/vitrectome) for the introduction of air.

Therefore, depending on the phase of surgery, the control unit controls the infusion system to infuse air at a controlled pressure or saline solution contained in the reservoir.

In one embodiment, the battery of taps connected to the cannula of the surgical instrument inserted in the eyeball is provided with an input for a saline solution and an inlet for the air, and the air-saline switching is performed by selecting the desired input.

The main advantage of the invented device compared to existing surgical instruments for eye surgery consists in the direct measurement of intraocular pressure by means of a detector inserted in the eye cavity. Unlike the indirect methods currently used, based on the measurement of the pressure or flow on the infusion/aspiration line, the direct approach permits measurement of the pressure value at any phase of surgery and not only during the operations carried out by the surgical instrument. Furthermore, the direct measurement takes into account possible variations in intraocular pressure related to external factors, such as scleral indentation or the injection of other fluids. These factors are not measured and compensated with the indirect measurement of pressure on the infusion line. The ability to monitor and compensate pressure variations occurring during eye surgery by direct measurement could potentially reduce the risks of intraoperative and postoperative complications (infection, bleeding, detachment of the retina or choroid), contributing to a more effective recovery of eyesight. These advantages would be most evident especially in patients with pathologies that compromise the perfusion of the optic nerve and the retina, who are more susceptible to intraocular pressure increases with consequent decreases in perfusion pressure.

The proposed invention also has substantial benefits compared to the device of the prior art for the direct measurement of pressure using a pressure detector mounted on the surgical instrument. Such system is more invasive because it requires ocular incisions of considerable diameter. In this application, the pressure detector is instead integrated with the endoilluminator, which has smaller dimensions than the surgical instruments, thus using a single incision of limited diameter (no larger than 25 gauge). For surgical procedures where the use of endoilluminators is not necessary, such as in trabeculectomy and cataract, the pressure detector is instead integrated with the infusor, by inserting it directly in the infusion cannula to limit the size of the incision. Another advantage over the device mounted on the surgical instrument consists of the greater accuracy of pressure measurement that is carried out in regions of the eye not disturbed by the action of the surgical instrument, inserted in a different part of the eye cavity from the detector.

A person skilled in the art may make modifications and variations to the embodiments of the surgical assembly, system and method of compensation of intraocular pressure according to the invention, replacing elements with others functionally equivalent so as to satisfy contingent requirements while remaining within the scope of protection of the following claims. Each of the characteristics described as belonging to a possible embodiment may be realised independently of the other embodiments described.

The invention claimed is:

1. A surgical assembly for ocular surgery comprising: a direct measuring device of intraocular pressure, a surgical accessory utilizable in conjunction with a surgical instrument suitable for performing eye surgery, the surgical accessory being insertable in an ocular cavity through an accessory ocular incision, wherein the direct measuring device of intraocular pressure is coupled to the surgical accessory so as to be insertable in the ocular cavity along with the surgical accessory through the accessory ocular incision; wherein the direct measuring device comprises a fiber optic pressure transducer; wherein the fiber optic pressure transducer extends inside an infusion cannula, and wherein the fiber optic pressure transducer and the infusion cannula are connected to each other by a three-way solenoid valve, the three-way solenoid valve having a first way being fluidically connected to the infusion cannula, a second way, aligned with the first way, being connected to a fiber optic pressure transducer with axial locking of the fiber optic pressure transducer, and a third way being fluidically connected to an output line of a fluid infusion pump.

2. The assembly of claim 1, wherein the surgical accessory is the infusion cannula of an infusion system, suitable for injecting an irrigation fluid for a compensation of intraocular pressure.

3. The assembly of claim 1, wherein the fiber optic pressure transducer, an optical fiber and an endo-illuminator are coupled to one another by an attachment guide ring in which the fiber optic pressure transducer, the optical fiber and the endo-illuminator are inserted with interference, the attachment guide ring being suitable for abutting with a flange of a positioning cannula positioned in an eyeball so as to determine an insertion depth of the fiber optic pressure transducer and the endo-illuminator in the eyeball.

4. The assembly of claim 1, wherein the fiber optic pressure transducer is inserted with interference in an attachment guide ring suitable for cooperating with the infusion cannula so as to determine a position of a distal end of the fiber optic pressure transducer relative to a distal end of the infusion cannula.

5. The assembly of claim 1, wherein the infusion cannula comprises a distal portion suitable for being inserted in an eyeball and a cylindrical proximal portion suitable for abutting with a flange of a positioning cannula positioned in the eyeball and suitable for receiving the distal portion of the infusion cannula with the fiber optic pressure transducer inserted.

6. The assembly of claim 1, wherein the fiber optic pressure transducer is inserted with interference in an attachment guide ring suitable for cooperating with the third way of the three-way valve so as to determine a position of a distal end of the pressure transducer relative to a distal end of the infusion cannula.

7. The assembly of claim 1, wherein the surgical accessory is an endo-illuminator device for illuminating a field of surgery.

8. The assembly of claim 7, wherein the endo-illuminator comprises an optical fiber or a chandelier probe.

* * * * *